US00PP08864P

United States Patent [19]

Kamada et al.

[11] Patent Number: Plant 8,864

[45] Date of Patent: Aug. 16, 1994

[54] MELROSE PLUM TREE

[75] Inventors: Leonard M. Kamada, Orange Cove; Ignacio Sanchez, Dinuba, both of Calif.

[73] Assignee: David K. Kamada, Reedley, Calif. ; a part interest

[21] Appl. No.: 148,678

[22] Filed: Nov. 4, 1993

[51] Int. Cl.[5] ..... A01H 5/00

[52] U.S. Cl. ..... Plt./38.1

[58] Field of Search ..... Plt. 68.1

*Primary Examiner*—James R. Feyrer

*Attorney, Agent, or Firm*—Worrel & Worrel

[57] ABSTRACT

A new and distinct variety of plum tree which is somewhat remotely similar to the "Black Beaut" plum tree in that it produces fruit which are mature for harvesting and shipment approximately simultaneously with the fruit of the "Beaut" plum tree, but from which it is distinguished by having a greater regularity of bearing, due to the production of pollen, and wherein the fruit has a more uniformly dark purple skin coloration, a more balanced flavor and a smaller pit without a tendency to fragment.

1 Drawing Sheet

BACKGROUND OF THE NEW VARIETY

The present invention relates to a new and distinct variety of plum tree, which will hereinafter be denominated varietally as the "Melrose" plum tree, and, more particularly, to a plum tree which produces semi-freestone fruit which are mature for commercial harvesting and shipment approximately June 1 to June 5 in the San Joaquin Valley of central California, having a firm flesh and a dark purple skin coloration.

It is implicit in the commercial production of tree fruit that new varieties will be discovered and will, over time, replace existing varieties. However, the recognition of this fact does not significantly assist in the selection of the replacement varieties. With many thousands of potential candidates, the selection process is an imposing challenge. Ultimately, the law of the marketplace determines which new varieties replace existing varieties, but initial determinations as to which candidates should be selected for further development require painstaking effort over many years of effort.

The "Black Beaut" plum tree has been a successful commercial variety, but has several notably unattractive characteristics. The "Black Beaut" plum tree is pollen sterile which results in an irregularity of bearing. The coloration of the skin of the fruit thereof is uneven and the flavor acidic. Still further, the stone of the fruit of the "Black Beaut" plum tree has a tendency to fragment within the flesh of the fruit. While the "Black Beaut" plum tree has, nonetheless, been commercially successful, the discovery of a new plum variety retaining the attractive attributes thereof while improving upon such unattractive characteristics would constitute a promising successor. The new varieity of the present invention appears to be such a candidate.

ORIGIN AND ASEXUAL REPRODUCTION OF THE NEW VARIETY

The present variety of plum tree hereof was discovered in an orchard of one of the inventors located in Orange Cove in the central San Joaquin Valley of California in 1986. The newly found mutation was a sport of the "Ambra" plum tree. The orchard in which the discovery took place is a planting of "Ambra" plum trees. The new variety was first asexually reproduced by Leonard M. Kamada in 1987 by grafting scions thereof onto root stock of the "Marianna" plum tree in the orchard of discovery. The inventors have continued to observe the asexually reproduced trees and have confirmed that they are in all respects identical to the parent tree.

SUMMARY OF THE NEW VARIETY

The plum tree of the present invention is characterized by producing a semi-freestone fruit which has a deep purple skin coloration and is ripe for commercial harvesting and shipment approximately June 1 to June 5 in the San Joaquin Valley of central California. The new variety is most closely similar to the "Black Beaut" plum tree, but is distinguishable therefrom by producing an oblate shaped fruit with recessed tip, whereas the "Black Beaut" plum tree has an ovate shape with a raised apex. The new variety has a uniform dark purple skin coloration, unlike that of the "Black Beaut" plum tree which is often poorly colored on the basal shoulders. The flavor of the new variety is well balanced, while the "Black Beaut" plum tree has a more acidic flavor. The new variety develops pollen in the anthers which makes the flowers more attractive to bees thereby developing a greater potential for regular cropping in comparison with the "Black Beaut" plum tree which is a pollen sterile plum tree resulting in difficulty obtaining good fruit set and causing irregularity in bearing. Furthermore, the new variety has a relatively small sized pit with no tendency to fragment, unlike the "Black Beaut" plum tree which has a medium sized pit prone to fragmentation during the final growth phase, leaving many pieces of the stone within the fruit. Such superior characteristics in the new variety make it an attractive candidate to replace the "Black Beaut" plum tree for commercial fruit production.

BRIEF DESCRIPTION OF THE DRAWING

The drawing is a color photograph showing mature fruit of the new variety of plum tree of the present invention illustrating the distinctive characteristics thereof including a first shown in side elevation so as to display the suture thereof; a second in side elevation; a third sectioned and laid open to expose the pit well in one section and with the stone left in place in the other section; a fourth in plan view oriented to expose the base thereof; a fifth in plan view oriented to expose the apex thereof; a stone of the fruit; and representative foliage, all of the new variety.

DETAILED DESCRIPTION

Referring more specifically to the pomological details of this new and distinct variety of plum tree, the following has been observed under the ecological conditions prevailing at the orchard of origin which is located in Orange Cove in the San Joaquin Valley of California. All major color code designations are by reference to the *Dictionary of Color,* by Maerz and Paul, First Edition, 1930. Common color names are also occasionally employed.

TREE

Generally: Hardy under typical San Joaquin Valley climatic conditions.

*Size.*—The tree produces over 121.92 cm (48 inches) of new growth in the top of the tree annually.

*Vigor.*—Vigorous.

*Figure.*—Upright to upright-spreading in form with high lateral spur density on upright shoots. The eventual form and density is determined by pruning. The tree is trained to a standard open vase system.

*Productivity.*—Productive.

*Regularity of bearing.*—Regular.

Trunk:

*Size.*—Medium thickness.

*Surface texture.*—Moderately rough with strong scarfskin development.

*Color.*—Brownish-grey (8-H-3).

*Lenticels — numbers.*—Numerous.

*Lenticels — size.*—Large, flat lenticels.

Branches:

*Size.*—Medium thickness.

*Surface texture.*—Medium-rough surface texture.

*Color — one year or older wood.*—Brown (8-L-7 Carbuncle Brown).

*Color — immature branches.*—Light green (19-K-6), darkening early in the season to a light brown (15-A-12 Burnt Umber).

LEAVES

Size:

*Generally.*—Medium. Leaf measurements are from vigorous shoots of current season's growth.

*Average length.*—13.5 cm (5.315 inches) to 14.2 cm (5.591 inches).

*Average width.*—5.2 cm (2.047 inches) to 5.8 cm (2.283 inches).

*Thickness.*—Average.

Form: Most frequently obovate, but with some lanceolate leaves occasionally present. Leaf apex is acuminate and most frequently reflexed downwards and slightly twisted sideways.

Color: New developing leaves are light yellow-green (19-K-3 Chrysolite Green) on the shoot tips.

*Upwardly disposed surface.*—Dark green (23-C-8).

*Downwardly disposed surface.*—Lighter grey-green (22-H-6).

Marginal form:

*Generally.*—Crenate. Moderately large, coarse crenations are present, at times doubly crenate and occasionally triply crenate near mid-margin.

Leaf margin: Very slightly undulate.

Petiole:

*Length.*—Ranges from 16 mm (0.6299 inches) to 18 mm (0.7087 inches).

*Thickness.*—Ranges from 1.5 mm (0.591 inches) to 2.0 mm (0.0787 inches).

*Color.*—Very pale green (19-I-5 Kildare Green) with tinges of rose red (4-A-10) Woodland Rose) along the ridges of the petiole groove.

Stem glands:

*Size.*—Medium.

*Form.*—Most frequently globose, although some variability exists.

*Position.*—From 2 to 5 stalked globose glands are present on the leaf petiole, alternate in position and 1 to 2 more glands, variable in form from globose to reniform, can be present on the basal margins of the leaf blade.

*Color.*—Bright green (20-L-3 Certose Green) when young, becoming substantially darker and brownish with age.

Stipules: A high percentage of the stipules are persistent well into the growing season.

*Size.*—Moderately long, from 8 mm (0.3150 inches) to 10 mm (0.3937 inches).

*Form.*—Linear lanceolate with serrate margins.

*Color.*—Light green (20-J-3 Shadow Green).

FLOWERS

Flower buds:

*Generally.*—Hardy under typical San Joaquin Valley climatic conditions.

*Size.*—Medium to small.

*Surface texture.*—Surfaces of the bud scales are very slightly pubescent.

*Form.*—Conic in form and plump. The buds are slightly appressed to the stem.

*Color.*—Dark chocolate brown (8-J-11 Montella Brown).

Date of bloom: Bloom is early in relation to other Japanese plum cultivars (Prunus salicina). The bloom of the new variety closely overlaps the bloom of the commercial plum cultivar, the "Catalina" plum tree (Unpatented). Date of first bloom was February 15 in 1993. Date of full bloom was February 23 in 1993.

Bloom quantity: Abundant and well distributed throughout the tree. The number of flowers per node is variable, from 2 to 6 flowers per node, most commonly 4.

Size:

*Generally.*—Medium, from 17 mm (0.6693 inches) to 23 mm (0.9055 inches) when fully expanded.

Petals:

*Color.*—Uniform white (1-A-1).

*Size.*—Medium.

*Length.*—8 mm (0.3150 inches) to 10 mm (0.3937 inches).

*Width.*—8 mm (0.3150 inches) to 9 mm (0.3543 inches).

*Form.*—Variable from obovate to nearly globose.

*Number.*—Five.

*Claw.*—Short and truncate.

*Margins.*—Undulate, somewhat ruffled near the apex.

*Apex.*—Very undulate and generally rounded.

Flower — pedicel: Medium.

*Length.*—3 mm (0.1181 inches) to 4 mm (0.1575 inches).

*Thickness.*—Averages 1 mm (0.0394 inches).

*Color.*—Pale green (19-J-2).
*Surface.*—Glabrous.
Nectaries:
*Color.*—Yellow-green (19-L-4) when young, becoming slightly darker with age.
Calyx:
*Surface.*—Glabrous.
*Color.*—Pale green (18-H-2) with light hues of red occasionally present.
Sepals:
*Size.*—Medium.
*Form.*—Generally oval, with a broad base and serrate margins.
*Color.*—Light green (18-H-2) with reddish hues present especially along the sepal margins.
Anthers:
*Size.*—Medium.
*Color.*—Gold-yellow (10-K-5) ventrally and light yellow-orange (11-H-8) dorsally with darker red (5-I-11) margins.
Pollen: Moderately abundant.
*Color.*—Yellow (9-L-3).
Stamens:
*Length.*—Variable, from 5 mm (0.1969 inches) to 7 mm (0.2756 inches). The longest stamens are approximately equal in length to the pistil.
Filament:
*Color.*—White (1-A-1).
Pistil:
*Color.*—Pale green (17-K-4).
*Surface texture.*—Glabrous.
*Length.*—Ranges from 7 mm (0.2756 inches) to 8 mm (0.3150 inches) including the ovary.

FRUIT

Maturity when described: Ripe for commercial harvesting and shipment approximately June 1 in 1992 to June 5 in 1992 near Orange Cove, Calif.
Size:
*Generally.*—Medium to large.
*Average diameter in the axial plane.*—Ranges from 43 mm (1.693 inches) to 49 mm (1.929 inches).
*Average diameter in the suture plane.*—Ranges from 56 mm (2.205 inches) to 60 mm (2.362 inches).
*Average diameter in the cheek plane.*—Ranges from 56 mm (2.205 inches) to 60 mm (2.362 inches).
Form:
*Uniformity.*—Highly uniform.
*Symmetry.*—Usually quite symmetrical. Oblate in lateral aspect and globose in apical aspect.
Suture:
*Generally.*—The suture is a distinct line, moderately deep, extending from base to apex. The suture is most distinct over the basal shoulder and inside the cavity basin. Suture color usually matches the general color of the fruit, having no distinct color of its own.
Ventral surface:
*Generally.*—Relatively smooth and only slightly lipped.
Stem cavity:
*Generally.*—Relatively broad and shallow.
*Width.*—Ranges from 27 mm (1.063 inches) to 30 mm (1.181 inches).
*Depth.*—Ranges from 11 mm (0.4331 inches) to 13 mm (0.5118 inches).
*Length.*—Ranges from 27 mm (1.063 inches) to 31 mm (1.220 inches).
*Shape.*—Variable from oval to nearly globose.
Stem:
*Color.*—Ranges from a light green (20-L-3 Certosa Green) to a light green-brown (13-L-5 Bistre Green).
Apex:
*Shape.*—Rounded with a depressed tip.
Pistil point:
*Position.*—The pistil point is apical and often has a slight callous spot present. The entire area on both sides of the apex is depressed.
Base: Usually moderately truncate and is most frequently at right angle to the fruit axis.
Skin: Tenacious to the flesh at commercial maturity.
*Thickness.*—Average.
*Texture.*—Glabrous.
*Tendency to crack.*—No observed tendency to crack.
*Surface.*—Slightly uneven or rippled.
*Flavor.*—Slightly acidic in taste.
*Color.*—Moderately uniform. Usually completely colored at commercial maturity. Primarily maroon-purple (8-J-6 Briarwood) with lighter, more reddish (7-J-5 Tapestry Red) areas usually near the basal end. The fruit surface is uniformly overlain with grey bloom.
Flesh color: Uniform pale yellow (10-G-2 Colonial Buff).
Surface of pit cavity: Slightly darker amber (9-H-4) color.
Flavor: Sweet with moderate acidity. Sugar to acid balance is good.
Aroma: Moderate amount of aroma is present.
Texture: Firm and fine textured.
Fibers:
*Numbers.*—Moderate number of light colored fibers present throughout the flesh.
*Texture. Tender.*
Ripening: Even.
Eating quality: Good.
Stone:
*Attachment.*—Semi-freestone, becoming more free with advancing maturity.
*Fibers — numbers.*—Numerous light colored fibers attached both laterally and along the stone sutures.
*Fibers — length.*—Short.
*Size.*—Relatively small and thin.
*Size — length.*—Ranges from 19.5 (0.7677 inches) to 22.0 (0.8861 inches).
*Size — width.*—Ranges from 17.5 mm (0.6890 inches) to 19.5 mm (0.7677 inches).
*Size — thickness.*—Ranges from 9.5 mm (0.3740 inches) to 12.0 mm (0.4724 inches).
*Form — generally.*—Somewhat irregular, but most frequently broadly ovate.
*Apex — shape.*—Generally rounded with a low tip.
*Color — dry.*—Variable, from a tan/chamois (11-F-4) to a darker cinnamon brown (12-F-7).
*Base — shape.*—Truncate. The base angle is somewhat variable, but most frequently slightly oblique to the stone axis.
*Sides — generally.*—Usually slightly unequal.
*Hilum.*—Sunken and heavily eroded.
*Hilum — size.*—Medium.
*Hilum — form.*—Narrow-oval.
*Surface.*—Moderately smooth laterally with a netted, pebbled surface. A few shallow grooves are present over the basal shoulders, converging basally.

*Ventral edge.*—Narrow with a strong wing present basally, protruding out 2.5 mm (0.0984 inches) to 3.0 mm (0.1181 inches) from the body of the stone.

*Dorsal edge.*—A distinct groove is present along the dorsal edge of the stone from base to apex, from 1.5 mm (0.0591 inches) to 2.0 mm (0.0787 inches) in width at mid-suture. The groove is less distinct as it approaches the apex. The groove is subtended by two narrow ridges which are occasionally cross-notched, especially over the apical shoulder.

*Tendency to split.*—None observed.

Use: Fresh market.

Keeping quality: High quality. Suitable for local markets as well as for long distance shipping.

Although the new variety of plum tree possesses the described characteristics noted above as a result of the growing conditions prevailing near Orange Cove in the central San Joaquin Valley of California, it is to be understood that variations of the usual magnitude and characteristics incident to changes in growing conditions, irrigation, fertilization, pruning, pest control, climatic variation and the like are to be expected.

Having thus described and illustrated our new variety of plum tree, what we claim as new and desire to be secured by Plant Letters Patent is:

1. A new and distinct variety of plum tree substantially as illustrated and described which is somewhat remotely similar to the "Black Beaut" plum tree, in that it produces fruit which are mature for commercial harvesting and shipment approximately June 1 to June 5 in the San Joaquin Valley of central California, or approximately simultaneously with the fruit of the "Black Beaut" plum tree, but which are distinguished therefrom in that, among other characteristics, the fruit has a more uniformly dark purple skin coloration and a more balanced flavor while having a greater regularity of bearing.

* * * * *

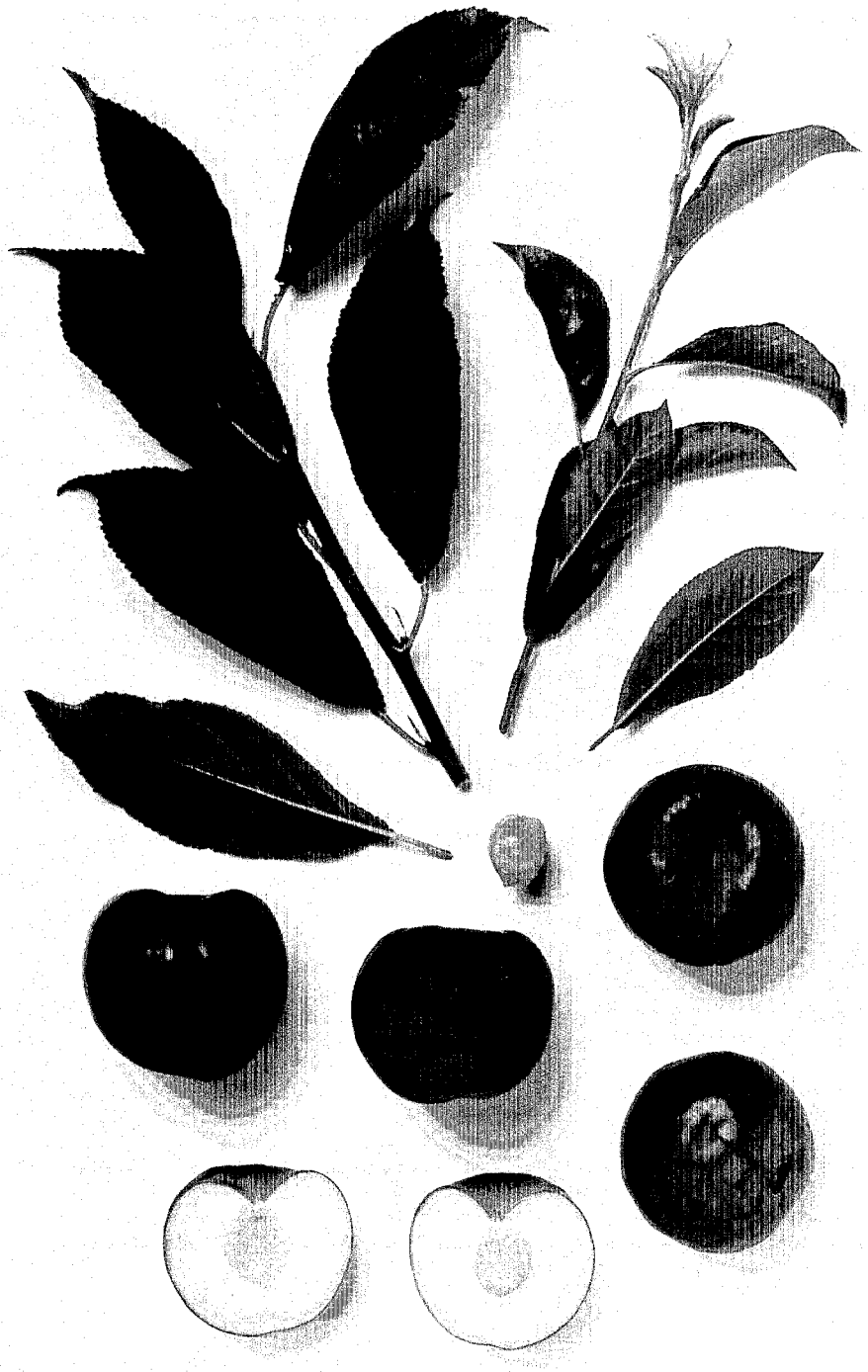

UNITED STATES PATENT AND TRADEMARK OFFICE

CERTIFICATE OF CORRECTION

PATENT NO. : PP 8,864

DATED : August 16, 1994

INVENTOR(S) : Leonard M. Kamada, Ignacio Sanchez

It is certified that error appears in the above-indentified patent and that said Letters Patent is hereby corrected as shown below:

Column 4, line 18, delete "Certose" and insert --Certosa --.

Signed and Sealed this

Eighth Day of November, 1994

*Attest:*

Bruce Lehman

BRUCE LEHMAN

*Attesting Officer*

*Commissioner of Patents and Trademarks*